United States Patent
Chang et al.

(10) Patent No.: US 8,741,615 B2
(45) Date of Patent: Jun. 3, 2014

(54) MAGNETIC NANOPARTICLE WITH BIOCOMPATIBILITY

(75) Inventors: Wen-Hsiang Chang, Taipei (TW);
Wen-Uan Hsieh, Jhubei (TW);
Shiu-Hua Huang, Jhonghe (TW);
Chin-I Lin, Yongkang (TW); Shian-Jy Jassy Wang, Jhudong Township, Hsinchu County (TW); Kelly Teng, Taipei (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 0 days.

(21) Appl. No.: 13/600,209

(22) Filed: Aug. 30, 2012

(65) Prior Publication Data
US 2012/0329129 A1   Dec. 27, 2012

Related U.S. Application Data

(62) Division of application No. 12/989,402, filed as application No. PCT/CN2008/000823 on Apr. 22, 2008, now abandoned.

(51) Int. Cl.
| | |
|---|---|
| C07F 7/18 | (2006.01) |
| C07K 16/00 | (2006.01) |
| C07K 2/00 | (2006.01) |
| C07H 23/00 | (2006.01) |
| C12N 9/96 | (2006.01) |

(52) U.S. Cl.
USPC ........ 435/188; 530/391.1; 530/409; 530/300; 530/395; 530/391.3; 556/419; 556/10; 536/53; 536/22.1; 428/402

(58) Field of Classification Search
None
See application file for complete search history.

(56) References Cited

U.S. PATENT DOCUMENTS

| | | | |
|---|---|---|---|
| 2004/0096507 A1 | 5/2004 | Kwang et al. | |
| 2006/0216239 A1 | 9/2006 | Zhang et al. | |
| 2007/0148095 A1* | 6/2007 | Chen et al. | 424/9.34 |
| 2007/0254005 A1* | 11/2007 | Pathak et al. | 424/423 |
| 2008/0089836 A1 | 4/2008 | Hainfeld | |

FOREIGN PATENT DOCUMENTS

| | | |
|---|---|---|
| CN | 1724076 A | 1/2006 |
| TW | 200724904 A | 7/2007 |
| WO | 2007136413 A2 | 11/2007 |

OTHER PUBLICATIONS

Examination opinion issued by the Taiwan Intellectual Property Office on Jul. 4, 2011, for the above-referenced application's counterpart application in Taiwan (Application No. 097101451).

* cited by examiner

*Primary Examiner* — Randy Gulakowski
*Assistant Examiner* — Jeffrey Washville
(74) *Attorney, Agent, or Firm* — Cesari and McKenna, LLP

(57) ABSTRACT

A magnetic nanoparticle is provided in the disclosure. The magnetic nanoparticle includes a magnetic nanoparticle; a biocompatible polymer of the following formula (II) covalently coupled to the magnetic nanoparticle, wherein $R_1$ is alkyl, aryl, carboxyl, or amino; n is an integer from 5 to 1000; and m is an integer from 1 to 10.

20 Claims, 2 Drawing Sheets

MAGNETIC NANOPARTICLE WITH BIOCOMPATIBILITY

CROSS REFERENCE TO RELATED APPLICATIONS

This application is a Divisional of U.S. patent application Ser. No. 12/989,402, filed Mar. 16, 2011 and entitled "Biocompatible polymer and magnetic nanoparticle with biocompatibility," which is a National Stage of International Application No. PCT/CN2008/000823, filed on Apr. 22, 2008. The contents of both prior applications are incorporated herein by reference in their entirety.

BACKGROUND OF THE INVENTION

1. Field of the Invention

The invention relates to a biocompatible polymer and in particular to a biocompatible polymer for covalently modifying magnetic nanoparticles.

2. Description of the Related Art

Magnetic resonance imaging (MRI) is an appealing non-invasive approach for early cancer diagnostics and therapeutics. MRI utilizes radio frequency pulses and magnetic field gradients applied to a subject in a strong field to produce images. MRI is capable of showing several different characteristics of tissues. The level of tissue magnetization at specific signal recording periods during the MR imaging cycle generally determines the brightness of a particular tissue in the MRI images. Contrast is produced when tissues do not have the same level of magnetization.

While the imaging capabilities of MRIs have revolutionized imaging technology, the resolution is limited to the elucidations of lesions within the body on the order of 1 mm. This limitation has led to the development of contrast enhancement agents. Because of the superparamagnetic property, iron oxide nanoparticles have been found effective as contrast enhancement agents for MRIs. The magnetic nanoparticle can be modified with a biocompatible polymer to prolong the particle circulation time in blood and reduce immunogenicity. Furthermore, the magnetic nanoparticle can be modified with a fluorescent dye and a specific targeting agent to provide fluorescent properties and specific targeting functions.

U.S. Patent Publication No. 20070148095 discloses a multi-modality contrast agent with specificity for both magnetic and optical imaging. The multi-modality contrast agent includes a magnetic nanoparticle, a biocompatible polymer chemically modifying the magnetic nanoparticle, a fluorescent dye coupled to the biocompatible polymer, and a specific targeting agent coupled to the biocompatible polymer. The biocompatible polymers include polyethylene glycol (PEG), polylactic acid (PLA), PLA-PEG, poly(glycolic acid) (PGA), poly(ε-caprolactone) (PCL), poly(methyl methacrylate) (PMMA), and the like.

U.S. Patent Publication No. 20070148095 discloses a silane compound for modifying magnetic nanoparticle and a method for using the nanoparticle to detect and treat tissues of interest.

Commercially available MRI contrast enhancement agents include Feridex® (dextran-coated iron oxide) and Resovist® (carboxydextran-coated iron oxide).

BRIEF SUMMARY OF THE INVENTION

In one aspect, the invention provides a biocompatible polymer of formula (I),

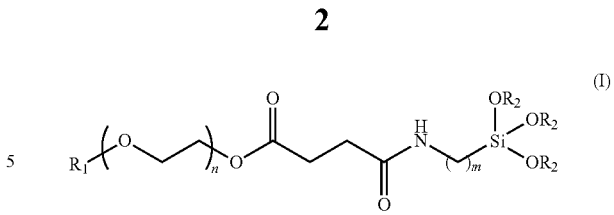

wherein $R_1$ is alkyl, aryl, carboxyl, or amino, $R_2$ is alkyl or aryl, n is an integer 5 to 1000, and m is an integer from 1 to 10.

In another aspect, the invention provides a magnetic nanoparticle with biocompatibility, comprising a magnetic nanoparticle and a biocompatible polymer of formula (II) covalently coupled to the magnetic nanoparticle,

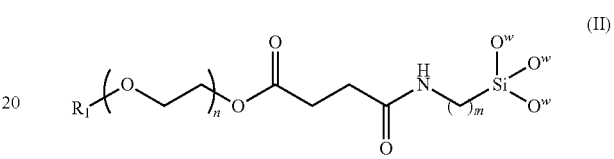

wherein $R_1$ is alkyl, aryl, carboxyl, or amino, n is an integer from 5 to 1000, and m is an integer from 1 to 10.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of invention and should not be taken in a limiting sense. The scope of the invention is best determined by reference to the appended claims.

Figure 1:
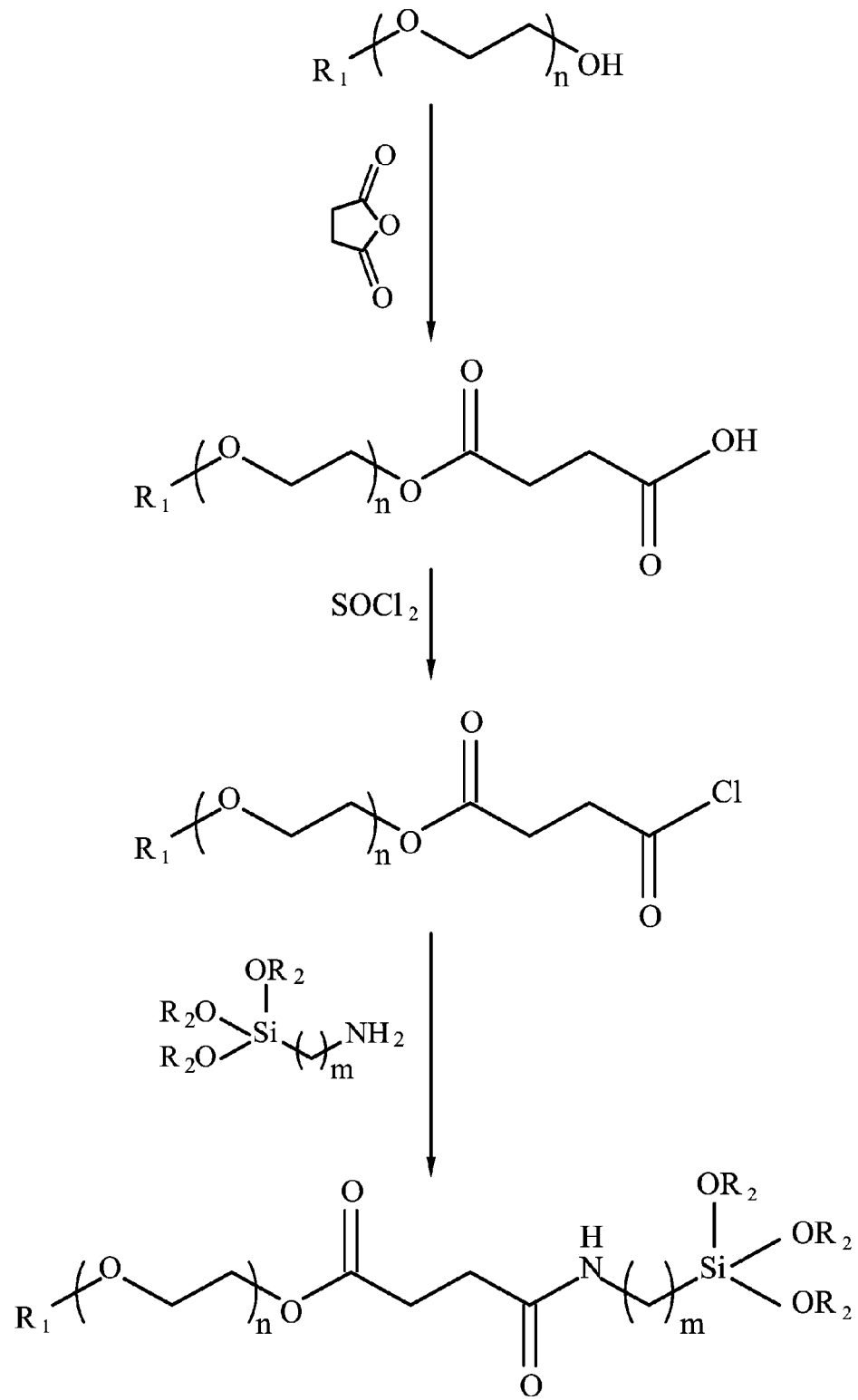
FIG. 1 is a schematic drawing showing the synthesis of the biocompatible polymer of the invention.

The biocompatible polymer of the invention is represented by general formula (I),

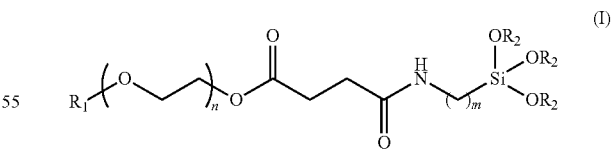

wherein $R_1$ is alkyl, aryl, carboxyl, or amino, $R_2$ is alkyl or aryl, n is an integer from 5 to 1000, and m is an integer from 1 to 10. FIG. 1 is a schematic drawing showing the synthesis of the biocompatible polymer of the invention, wherein R1, R2, n, and m have the same meaning as described above. As shown in FIG. 1, the synthetic scheme involves converting the hydroxyl end group of polyethylene glycol (PEG) to a carboxyl group by using a succinic anhydride compound, and coupling a silane group to the PEG. Suitable alkyl groups for $R_1$ and $R_2$ include $C_1$-$C_{20}$ straight chain or branched alkyl groups. In one embodiment, each of $R_1$ and $R_2$ independently, is a $C_1$-$C_6$ straight chain or branched alkyl such as methyl, ethyl, propyl, isopropyl, n-butyl, sec-butyl, tert-butyl, n-pentyl, isopentyl, tert-pentyl, n-hexyl, and isohexyl. Suitable aryl groups for $R_1$ and $R_2$ include $C_6$-$C_{12}$ substituted or unsubstituted aryl groups such as phenyl, biphenyl, and naphthyl, and examples of substituents thereof include hydroxyl, haloalkyl, alkoxyl, cyano, nitro, amino, or alkylamino. The number of methylene units m is preferably an integer from 1 to 10. The number of oxyethylene units n is preferably an integer from 5 to 1000, equivalent to a molecular weight of about 200-50000 g/mole of the PEG. In one embodiment, m is about 3, and n is about 15.

The biocompatible polymer synthesized in FIG. 1 is useful in that it can chemically modify the surface of the iron oxide nanoparticle to increase biocompatibility. In addition, the biocompatible polymer is useful in that it can label particles (e.g., nanoparticles, magnetic particles, magnetic nanoparticles, superparamagnetic particles), to render the particles to be further reactive toward one or more targeting, fluorescent, therapeutic, or diagnostic agents.

The invention also provides a magnetic nanoparticle with biocompatibility, comprising a magnetic nanoparticle; a biocompatible polymer of formula (II) covalently coupled to the magnetic nanoparticle,

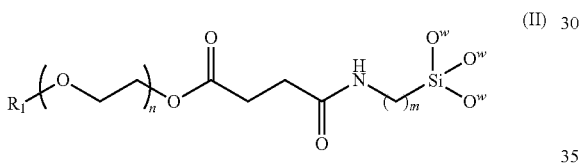

Figure 2:
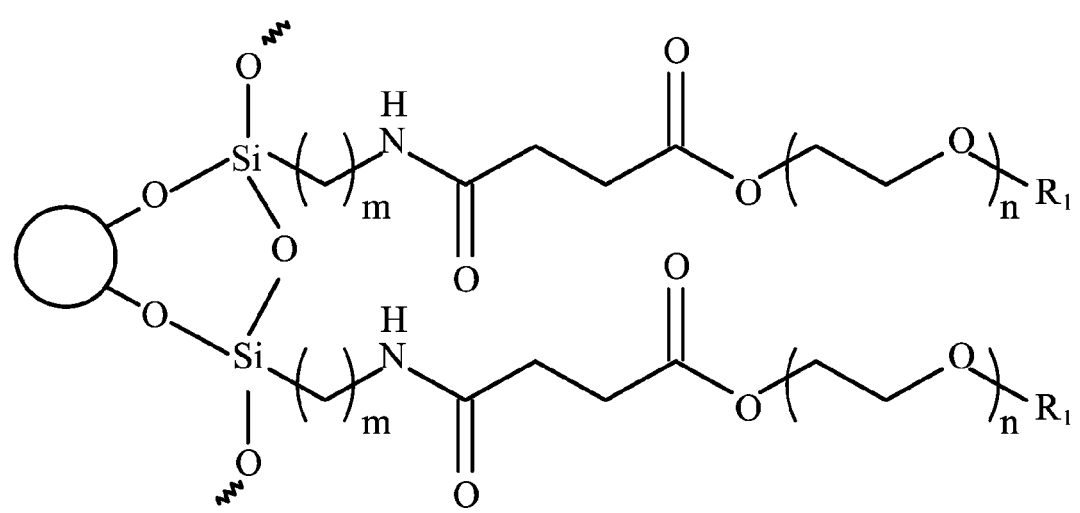
FIG. 2 is a schematic drawing showing a magnetic nanoparticle modified with the biocompatible polymer of the invention.

(II)

wherein $R_1$ is alkyl, aryl, carboxyl, or amino, n is an integer from 5 to 1000, and m is an integer from 1 to 10. FIG. 2 is a schematic drawing showing a magnetic nanoparticle modified with the biocompatible polymer of the invention. The magnetic nanoparticle is preferably made of at least one of Fe, Co, Ni, and oxides thereof. It will be appreciated that the nanoparticle can be made of any single or composite magnetic material, although superparamagnetic materials are particularly preferred. After the biocompatible polymer is chemically bonded to the magnetic nanoparticle, the terminal groups $R_1$ are transformed into active functional groups such as carboxyl or amino groups to allow coupling with fluorescent dye and/or specific targeting agents. However, $R_1$ is not alkyl or aryl, since alkyl or aryl are not capable of coupling with targeting agents or fluorescent dye. In one embodiment, $R_1$ is a carboxyl group. The number of methylene units m is preferably an integer from 1 to 10. The number of oxyethylene units n is preferably an integer from 5 to 1000. In one embodiment, m is about 3, and n is about 15. The biocompatible polymer is preferably coated on the entire surface of the magnetic nanoparticle to form a core-shell structure. More preferably, the biocompatible polymer forms a monolayer coating on the magnetic nanoparticle.

Experimental results indicate that the biocompatible polymer of the invention may increase the r2 value of the magnetic nanoparticle to about 2 times that of commercial contrast agents, Feridex® and Resovist®. Accordingly, the magnetic nanoparticle may provide greater contrast enhancement when being used as an MRI contrast agent.

The targeting agent is preferably coupled to the biocompatible polymer via covalent bonds. Commonly used targeting agents include an antibody, a protein, a peptide, an enzyme, a carbohydrate, a glycoprotein, a nucleotide, and a lipid. The magnetic nanoparticle may have a diameter of about 3-500 nm after coupling with the targeting agent. Those skilled in the art can attach any suitable targeting agents on the nanoparticle to give specificity thereto. For example, folic acid can be used to specify breast cancer cells with a folate receptor. The structure of the folic acid allows coupling with an amine-terminated or carboxy-terminated biocompatible polymer. For example, the folic acid allows coupling with the amine-terminated biocompatible polymer by forming a —CONH— linkage.

A fluorescent dye may be further coupled to the magnetic nanoparticle to provide an optical signal for optical imaging techniques such as NIR imaging, thus allowing real-time monitoring of foci by different imaging techniques. Preferably, the fluorescent dye is coupled to the biocompatible polymer via covalent bonds. Suitable fluorescent dyes include organic or inorganic dyes and organometallic complexes. The excitation and emission wavelengths of the fluorescent dye may be ultraviolet (UV), near-infrared (NIR), or visible (VIS) light. The magnetic nanoparticle coupled with the targeting agent and fluorescent dye preferably has a diameter of about 15-200 nm.

Without intending to limit the present invention in any manner, the present invention will be further illustrated by the following examples.

Example 1

Nanoparticle Preparation 11.6 g (0.058 mole) of $FeCl_2 \cdot 4H_2O$, 11.6 g (0.096 mole) of $FeCl_3 \cdot 6H_2O$ and 400 ml of deionized water were stirred in a three-necked flask at 300 rpm at 25° C. 170 ml of a 2.5N NaOH solution was added to the flask at a rate of 47 μl/sec. When a pH value of 11-12 was measured after the addition of the 2.5N NaOH solution, 20 ml of oleic acid was added and stirred for 30 minutes. Thereafter, a 6N HCl solution was slowly added to adjust the pH value to about 1, thus precipitating oleic acid encapsulated-iron oxide particles. The precipitates were collected, washed with deionized water for 4-5 times to remove excess oleic acid, and dried.

Example 2

Synthesis of Biocompatible Polymer mPEG-Silane 300 g (0.4 mole) of methoxy-PEG (mPEG, molecular weight: 750) and 600 ml of N-methyl-2-pyrrolidone were placed in a 1000 ml round bottom flask under vacuum (20 Ton) for more than 2 hours. 48 g (0.48 mole) of succinic anhydride and 19.5 g (0.159 mole) of 4-dimethylamino-pyridine (DMAP) were added for reaction at 30° C. for two days.

36 ml (0.48 mole) of thionyl chloride was added at a rate of 1 ml/min and the mixture was stirred for 2-3 hours. Thereafter, 133.8 ml (0.96 mole) of triethylamine was added at a rate of 1 ml/min. After cooled to room temperature, the mixture was filtered to remove precipitates. 94.5 ml (0.4 mole) of 3-aminopropyl triethoxysilane was added for reaction for at least 8 hours.

The reaction mixture was added to 9 L of isopropyl ether for re-precipitation, and the precipitates were collected, re-dissolved in 500 ml of toluene, and centrifuged at rpm for 5 minutes to collect a supernatant. The supernatant was again, added to 9 L of isopropyl ether for re-precipitation. Brown oily liquid was collected and dried under vacuum to obtain the biocompatible polymer, mPEG-silane.

Example 3

Synthesis of Biocompatible Polymer COOH-Peg-Silane 300 g (0.4 mole) of PEG (molecular weight: 750) and 600 ml of N-methyl-2-pyrrolidone were placed in a 1000 ml round bottom flask under vacuum (20 Torr) for more than 2 hours. 96 g (0.96 mole) of succinic anhydride and 39 g (0.318 mole) of 4-dimethylamino-pyridine (DMAP) were added for reaction at 30° C. for two days, thus obtaining dicarboxy-terminated PEG (COOH-PEG).

36 ml (0.48 mole) of thionyl chloride was added at a rate of 1 ml/min and stirred for 2-3 hours. Thereafter, 133.8 ml (0.96 mole) of triethylamine was added at a rate of 1 ml/min. After cooled to room temperature, the mixture was filtered to remove precipitates. Then, 94.5 ml (0.4 mole) of 3-aminopropyl triethoxysilane was added for reaction for at least 8 hours.

The reaction mixture was added to 9 L of isopropyl ether for re-precipitation, and the precipitates were collected, re-dissolved in 500 ml of toluene, and centrifuged at 5000 rpm for 5 minutes to collect a supernatant. The supernatant was again, added to 9 L of isopropyl ether for re-precipitation. Brown oily liquid was collected and dried under vacuum, thus obtaining the biocompatible polymer, COOH-PEG-silane.

Example 4

Coupling with Biocompatible Polymer 250 g of mPEG-silane or COOH-PEG-silane was added to 1-1.2 L of a toluene solution containing 10 g of iron oxide of Example 1 and the mixture was sonicated for 2-3 hours. After addition of 1.5 L of deionized water, the mixture was purified by an ultra-device and concentrated to 100 ml to obtain iron oxide nanoparticles modified by a biocompatible polymer.

Example 5

Coupling with Targeting Agent

226 µl of folate solution (folate/dimethyl sulfoxide: 10 mg/ml) was placed in a 50 ml brownish round bottom flask. 5 ml of dimethyl sulfoxide (DMSO) and 176.5 µl of dicyclohexyl carbodiimide solution (dicyclohexyl carbodiimide/DMSO: 5 mg/ml) was added to the solution and stirred for 1 hour. Thereafter, 98.5 µl of NHS solution (N-hydroxysuccinimide/DMSO: 5 mg/ml) was added and stirred for 1 hour. Then, 289 µl of ethylenediamine was added to give a solution A.

1 ml of the COOH-PEG-silane modified iron oxide nanoparticle of Example 4 (4.48 mg/ml) and 10 ml of DMSO were placed in a 50 ml round bottom flask under vacuum for 1 hour. 176.5 µl of dicyclohexyl carbodiimide solution (dicyclohexyl carbodiimide/DMSO: 5 mg/ml) was added to the solution and stirred for 1 hour. Thereafter, 98.5 µl of NHS solution (N-hydroxysuccinimide/DMSO: 5 mg/ml) was added and stirred for 1 hour to give a solution B.

2895 µl (half-volume) of solution A was added to solution B and stirred for 8 hours. The resulting solution was added into a dialysis membrane (Mw: 3000) and water was used for dialysis. Then, the solution was concentrated to 2 ml by an ultra-filtration device to obtain iron oxide nanoparticles coupled with a targeting agent.

Example 6

Coupling with Fluorescent Dye 1 ml of CypHer5 e (NIR dye from Amersham Bioscience Co., $10^{-6}$ mole/ml) was mixed with $10^{-6}$ mole of ethylenediamine and stirred for 1 hour, thus giving a solution C.

The iron oxide nanoparticles coupled with folate (2 mg/ml) of Example 5 were in 10 ml of deionized water, followed by addition of $10^{-6}$ mole of 1-ethyl-3-(3-dimethylaminopropyl) carbodiimide (EDC). After the mixture was stirred for one hour, $10^{-6}$ mole of N-hydroxysuccinimide (NHS) was added and stirred for another hour, thus giving a solution D.

Solution C was added to solution D and stirred for 8 hours. The resulting solution was added into a dialysis membrane (Mw: 3000) and water was used for dialysis. Then, the solution was concentrated to 2 ml by an ultra-filtration device to obtain iron oxide nanoparticles coupled with a targeting agent and a fluorescent dye.

Example 7

Relaxivity Test

The modified iron oxide nanoparticles of Example 5 were compared for the r1 and r2 relaxivity with the product of U.S. Patent Publication No. 2006/0216239 and commercial contrast agents, i.e., Feridex® and Resovist®.

Iron oxide solutions of various concentrations (0.1, 0.2, 0.3, 0.4, 0.5 mM) were prepared and measured for the T1 or T2 relaxation time by a Minispec mq 20 from the Bruker Corporation. A linear relationship was established between the reciprocal of relaxation time as the ordinate axis and the concentration of the solution as the abscissa axis. The slope of the linear relationship was the r1 and r2 relaxivity.

As shown in Table 1, the r2 relaxivity of the modified iron oxide nanoparticles of the invention was about 2 times that of Feridex® and Resovist®, and about 1.4 times that of the prior art product of U.S. Patent Publication No. 2006/0216239. Accordingly, the contrast enhancement was improved due to the higher r2 relaxivity.

TABLE 1

|  | The invention | US 2006/ 0216239 | Resovist ® | Feridex ® |
|---|---|---|---|---|
| Diameter* | 8-12 nm | 8-12 nm | 4.2 nm | 4.8-5.6 nm |
| r2 $(mM \cdot s)^{-1}$ | 321.8 ± 2.3 | 229 | 164 | 160 |
| r1 $(mM \cdot s)^{-1}$ | 33.4 ± 0.3 | 23.6 | 25.4 | 40 |

*The diameter was determined by TEM

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biocompatible magnetic material comprising:
   a magnetic nanoparticle; and
   a biocompatible polymer of formula (II) covalently coupled to the magnetic nanoparticle:

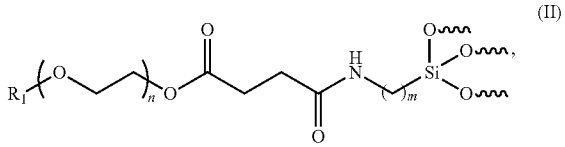

wherein the magnetic nanoparticle is an iron oxide; $R_1$ is alkyl, aryl, carboxyl, or amino; m is an integer from 1 to 10; and n is an integer from 5 to 1000.

2. The biocompatible magnetic material of claim 1, wherein $R_1$ is carboxyl or amino.

3. The biocompatible magnetic material of claim 1, wherein the magnetic nanoparticle is a superparamagnetic nanoparticle.

4. The biocompatible magnetic material of claim 2, wherein $R_1$ is coupled to a specific targeting agent, the specific targeting agent being an antibody, a protein, a peptide, an enzyme, a carbohydrate, a glycoprotein, a nucleotide, or a lipid.

5. The biocompatible magnetic material of claim 4, wherein the magnetic nanoparticle has a diameter of about 3-500 nm.

6. The biocompatible magnetic material of claim 4, wherein the biocompatible polymer is coupled to a fluorescent dye.

7. The biocompatible magnetic material of claim 6, wherein the biocompatible magnetic material has a diameter of about 15-200 nm.

8. The biocompatible magnetic material of claim 6, wherein the fluorescent dye exhibits at least one of ultraviolet, near-infrared, and visible light excitation or emission wavelength.

9. The biocompatible magnetic material of claim 6, wherein the fluorescent dye is an organic dye, an inorganic dye, or an organometallic complex.

10. The biocompatible magnetic material of claim 6, wherein the fluorescent dye and the specific targeting agent are coupled to the biocompatible polymer by a covalent bond.

11. The biocompatible magnetic material of claim 6, wherein the specific targeting agent and the biocompatible polymer are coupled by a —CONH— linkage.

12. The biocompatible magnetic material of claim 1, wherein the biocompatible polymer is coated on the magnetic nanoparticle to form a core/shell structure.

13. The biocompatible magnetic material of claim 12, wherein the biocompatible polymer forms a monolayer coating on the magnetic nanoparticle.

14. A biocompatible magnetic material comprising:
a magnetic nanoparticle; and
a biocompatible polymer of formula (II) covalently coupled to the magnetic nanoparticle:

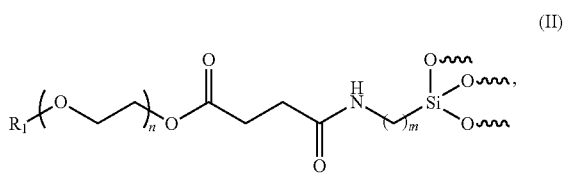

wherein the magnetic nanoparticle has an $R_2$ relaxivity of 319.5 $(mM \cdot s)^{-1}$ or greater; $R_1$ is alkyl, aryl, carboxyl, or amino; m is an integer from 1 to 10; and n is an integer from 5 to 1000.

15. The biocompatible magnetic material of claim 14, wherein $R_1$ is coupled to a specific targeting agent, $R_1$ being a carboxyl or amino group, and the specific targeting agent being an antibody, a protein, a peptide, an enzyme, a carbohydrate, a glycoprotein, a nucleotide, or a lipid.

16. The biocompatible magnetic material of claim 15, wherein the biocompatible polymer is coupled to a fluorescent dye that exhibits at least one of ultraviolet, near-infrared, and visible light excitation or emission wavelength.

17. The biocompatible magnetic material of claim 16, wherein the biocompatible magnetic material has a diameter of about 15-200 nm.

18. The biocompatible magnetic material of claim 16, wherein the fluorescent dye and the specific targeting agent are coupled to the biocompatible polymer by a covalent bond.

19. The biocompatible magnetic material of claim 16, wherein the magnetic nanoparticle is an iron oxide.

20. The biocompatible magnetic material of claim 14, wherein the biocompatible polymer is coated on the magnetic nanoparticle to form a core/shell structure.

\* \* \* \* \*